US006962691B1

(12) United States Patent
Lulla et al.

(10) Patent No.: US 6,962,691 B1
(45) Date of Patent: Nov. 8, 2005

(54) TOPICAL SPRAY COMPOSITIONS

(75) Inventors: Amar Lulla, Colaba (IN); Geena Malhotra, Mazgaon (IN); Preeti Raut, Vile Paele (IN)

(73) Assignee: U & I Pharmaceuticals Ltd., Long Island City, NY (US)

( * ) Notice: Subject to any disclaimer, the term of this patent is extended or adjusted under 35 U.S.C. 154(b) by 0 days.

(21) Appl. No.: 09/503,843

(22) Filed: Feb. 15, 2000

(30) Foreign Application Priority Data

| May 20, 1999 | (IN) | ............................. 382/BOM/99 |
| Aug. 17, 1999 | (IN) | ......................... 582/BOM/2000 |
| Jan. 13, 2000 | (IN) | ........................... 43/BOM/2000 |
| Jan. 13, 2000 | (IN) | ........................... 44/BOM/2000 |

(51) Int. Cl.[7] .............................................. A61L 9/04
(52) U.S. Cl. .......................... 424/45; 424/81; 424/448; 424/434
(58) Field of Search ........................... 424/45, 81, 448, 424/434

(56) References Cited

U.S. PATENT DOCUMENTS

| 3,476,853 A | | 11/1969 | Jatul et al. | |
| 3,932,602 A | * | 1/1976 | Sweger ........................ | 424/45 |
| 4,293,542 A | | 10/1981 | Lang et al. | |
| 4,316,887 A | * | 2/1982 | Kamishita et al. ............ | 424/81 |
| 4,534,958 A | | 8/1985 | Adams et al. | |
| 4,704,406 A | | 11/1987 | Stanislaus et al. | |
| 4,826,677 A | | 5/1989 | Mueller et al. | |
| 5,413,792 A | | 5/1995 | Ninomiya et al. | |
| 5,474,783 A | | 12/1995 | Miranda et al. | |
| 5,725,491 A | | 3/1998 | Tipton et al. | |
| 5,980,921 A | | 11/1999 | Biedermann et al. | |

FOREIGN PATENT DOCUMENTS

| CA | 1175355 | 4/1981 |
| EP | 0 055 396 | 7/1982 |
| EP | 0055397 | 7/1982 |
| EP | 0055397 A1 | 7/1982 |
| EP | 0356196 A2 | 2/1990 |
| EP | 390 541 | 10/1990 |
| EP | 0 521 455 | 1/1993 |
| EP | 0 617 972 | 10/1994 |
| EP | 0619115 A1 | 12/1994 |
| EP | 0679390 A2 | 2/1995 |
| EP | 0679390 | 11/1995 |
| EP | 713 708 | 5/1996 |
| EP | 0761095 A2 | 12/1997 |
| GB | 1372721 | 11/1974 |
| WO | WO 88/09185 | 12/1988 |
| WO | WO 96/30000 | 10/1996 |
| WO | WO 96/33689 | * 10/1996 |
| WO | WO 97/01327 | 1/1997 |
| WO | WO 0 756 870 | 5/1997 |
| WO | WO 98/23291 | 6/1998 |
| WO | WO0010540 | 3/2000 |

OTHER PUBLICATIONS

Jenny McElroy, "Victorian School of Pharmacy develops spray-on drugs," New Zealand Pharmacy, p. 3, Nov. 1999.
"Isocard Transdermal Spray", ABPI Compendium of Data Sheets and Summaries of Product Characteristics p. 306.

* cited by examiner

*Primary Examiner*—Christopher S. F. Low
*Assistant Examiner*—Amy Lewis
(74) *Attorney, Agent, or Firm*—Venable LLP; Julie A. Petruzzelli; Keith G. Haddaway

(57) ABSTRACT

A topical, medicinal spray composition is provided comprising a drug or combination of drugs in a carrier which, when sprayed on a surface, forms a film. The composition comprises at least one medicament, at least one film former and at least one vehicle. The composition of the invention may further comprise at least one permeation enhancer, at least one solubilizer, at least one plasticizer, and at least one water soluble additive. A metered dose of the composition can be sprayed on a topical site to form a stable, breathable film, preferably over a fixed surface area. A wide range of medicaments for human and veterinary use may be present that act locally or transdermally.

3 Claims, No Drawings

TOPICAL SPRAY COMPOSITIONS

BACKGROUND OF THE INVENTION

1. Field of the Invention

This invention relates to compositions for topical application of pharmaceutical compounds. Specifically, the invention relates to topical medicinal spray compositions, their use and films formed upon use. The compositions may be used to treat a variety of disorders.

2. Background of the Invention

Many delivery systems for the topical application of pharmaceutical compounds are currently available and include lotions, creams, gels, ointments, transdermal patches and sprays. The choice of delivery system usually depends upon the desired pharmacokinetic profile of the drug, for example, whether immediate or sustained release is required. Many of these systems suffer from occlusion problems and may cause skin irritation. For example, many compounds, including hormonal drugs, are conventionally delivered using a transdermal patch. These patches comprise an occlusive backing membrane which often results in local skin irritation. A further disadvantage of transdermal patches is that percutaneous penetration of the drug is often poor.

The problem of skin irritation associated with transdermal patches is not as pronounced when topical spray formulations are used. For example, British Patent Specification No. 1,372,721 discloses a container of antiseptic for the topical treatment of burns and scalds, containing a topically acceptable antiseptic active agent against *Pseudomonas aeruginosa*, a pressuring agent and at least one surfactant admixed with water. The container comprises an outlet, and valve means operable to allow discharge of the contents of the container through the outlet in the form of a foam which is effective in the control of *Pseudomonas aeruginosa* at the site of a burn or scald. U.S. Pat. No. 4,534,958 describes and claims "a sprayable aerosol foam treatment composition which is a liquid in the aerosol container and forms a gel upon application to the skin". The composition in U.S. Pat. No. 4,534,958 comprises water, propellant, volatile solvent, a polyoxyethylene copolymer whose function is not described, and optionally a burn treatment agent and one or more adjuvants. The composition is used "for treating living skin".

However, conventional topical spray formulations tend to remain at the application site for only a short time. For example, they are easily rubbed off. As a result, the medicament to be absorbed through the skin is only available transiently. By contrast, medicament in a transdermal patch is potentially available for as long as the patch remains in place.

This invention provides advantages not previously realized. Specifically, the invention provides a composition for the topical application of pharmaceutical compounds without causing occlusion problems or skin irritation. Moreover, the inventive compositions remove the need for an adhesive patch. The invention further provides a topically applied composition that may remain as a breathable film on the skin for an extended period of time.

SUMMARY OF THE INVENTION

Through this invention, the advantages offered by transdermal patches and topical sprays have been combined, while the disadvantages associated with each have been minimized. This invention relates to a topical spray composition which can be sprayed onto the skin to form a breathable film or patch, which remains stable and in place over a period of days. In this way, a medicament can be delivered transdermally over a period of time. Since the film is non-occlusive, the problem of local skin irritation associated with transdermal patches is substantially reduced.

The invention provides a composition for topical application of one or more medicaments, comprising at least one medicament for systemic or topical availability, at least one film former, and one or more vehicles. The composition contains preferably up to about 30% of the at least one medicament, more preferably up to about 10% of the at least one medicament and most preferably up to about 5% of the at least one medicament. The composition may further comprise one or more additional components selected from the group consisting of permeation enhancers, solubilizers, plasticizers, and water soluble additives, including humectants. Medicaments in the composition may be present in a form that is solubilized or suspended. After application, the medicaments may be locally or transdermally available and may be released from the composition. A wide range of medicaments for human or veterinary use may be used in the composition and the medicament may be present in chiral form. The compositions are preferably in a form suitable for application by spraying from an aerosol or pump spray container.

The invention further provides a stable, breathable film formed by applying the inventive compositions. The film is preferably formed over a fixed surface area. The fixed surface area is preferably less than about 50 cm$^2$ and more preferably from about 10 cm$^2$ to about 25 cm$^2$. Medicaments of the composition may be locally or transdermally available for release from the film.

Moreover, the invention comprises a method of using the inventive compositions pursuant to which a metered dose of the composition is dispensed onto an intended application site. The intended application site is preferably skin, and the metered dose is preferably applied over a fixed surface area. The fixed surface area is preferably less than about 50 cm$^2$ and more preferably from about 10 cm$^2$ to about 25 cm$^2$. The metered dose of the composition is preferably dispensed by spraying the composition from a pump or aerosol spray dispenser. In one embodiment, the composition forms a stable, breathable film on the intended application site after dispensing.

The above objectives and advantages of the invention are illustrative, and not exhaustive, of those which can be achieved by the invention. The examples presented herein are non-limiting.

DETAILED DESCRIPTION OF THE INVENTION

In describing the invention, the following definitions are applicable throughout.

"Breathable film" refers to a film formed on the surface of the skin that does not interfere with perspiration, respiration and other metabolic activities of the skin.

"Film-formers" refers to compounds, preferably polymers, that form stable films on a surface when applied. Within the meaning of the present invention, a film is stable if it is resistant to removal by rubbing for an extended period of time. The extended period of time is preferably at least about 24 hours and most preferably from about 1 day to about 5 days.

"Topical application" refers to being applied to a surface such as skin.

"Topically active" refers to the composition or medicament for topical application which treats predominately the surface on which it is applied.

"Percutaneous penetration" or "transdermally available" means that the medicament of the composition is absorbed through skin when applied topically. Typically, although not necessarily, the medicament will then be distributed throughout the body resulting in systemic action as opposed to being only locally active.

"Permeation Enhancer" refers to a component used to enhance the penetration rate of drugs through the skin, preferably by temporarily diminishing the impermeability of the skin. Permeation enhancers have also been called "accelerants" and "sorption promoters." Examples of permeation enhancers include lipophilic solvents, surfactants, menthol, fatty acid esters and polyhydric alcohols.

"Plasticizer" refers to a component that aids a composition in forming a flexible, adherent film on the skin. Examples of plasticizers include citrate esters, dimethyl isosorbide, castor oil, propylene glycol and polyethylene glycol.

"Solubilizer" refers to components that aid in the dissolution or dispersement of the drug in the formulation. Examples of solubilizers include acrylate and methacrylate ester polymers and copolymers, surfactants, polyhydric alcohols, Vitamin E, Vitamin E TPGS and labrasol.

The present invention includes a topical, medicinal spray composition comprising a drug or combination of drugs as a solution or suspension in a vehicle optionally containing a polymer or combination of polymers which, when sprayed on the surface of the skin, forms a film on the skin. The compositions of the invention preferably comprise up to about 30% of at least one medicament (e.g., 0.0001% to about 30%), more preferably up to about 10% of at least one medicament (e.g., 0.0001% to about 10%) and most preferably up to about 5% of at least one medicament (e.g., 0.0001% to about 5%) dissolved or suspended in one or more vehicles which comprise up to 90% of the composition (e.g., 0.0001% to about 90%). The composition may further contain one or more film former, solubilizer, permeation enhancer and plasticizer. The composition may contain one or more of these additives in amounts of up to about 10% film-former (e.g., 0.0001% to about 10%), up to about 10% solubilizer (e.g., 0.0001% to about 10%), up to about 8% permeation enhancer (e.g., 0.0001% to about 8%), and up to about 10% plasticizer (e.g., 0.0001% to about 10%). The inventive composition may be sprayed on a topical site to form a stable, breathable film on the site, from which film the medicaments act locally on the surface or are transdermally available. Preferably, the composition further comprises up to about 7% (w/w) of one or more water-soluble additives (e.g., 0.0001% to about 7%). The drug or combination of drugs so deposited in the matrix of the film-former may remain solubilized or suspended. The exact formulation of the composition may vary depending on the nature of the particular medicament used (for example, the solubility profile) and the release profile desired. The compositions can be dispensed from any dispenser, preferably a dispenser which provides the composition as a spray, and may be used for systemic action or topical action. The drug from the composition may be released over a period of time or immediately.

The compositions of the present invention are preferably applied in a metered dose over a predetermined surface area. Accordingly, the present invention may also provide for the administration of the composition by spraying the composition from a dispenser. The invention further provides a method for applying the composition and the resultant film.

Preferably, the composition is dispensed from a pump dispenser or from an aerosol dispenser. In the latter case, the composition additionally comprises from about 10% to 90% of propellant in order to provide a suitable pressure within the aerosol dispenser. Generally, propellant is not required for compositions dispensed from a pump dispenser. However, if desired, such compositions may also comprise from about 10% to 90% of a propellant which is liquid at room temperature, for example, trichloromonofluoromethane (P11).

The invention also provides a method of preparing a pump dispenser containing the spray composition of the invention comprising mixing the ingredients of the composition with or without liquid propellant and placing the mixed ingredients in a pump dispenser.

In addition, the invention provides a method of preparing an aerosol dispenser containing the spray composition of the invention comprising mixing the ingredients of the composition without propellant and charging the mixture together with propellant into an aerosol dispenser. The composition is preferably dispensed from the chosen dispenser in a metered dose.

The medicament can be any medicinal compound in the salt or base form or a combination of compounds which is stable on mixing with the other ingredients of the composition and effective on topical administration. The medicament is preferably a drug which is an anti-emetic, an anti-anginal, an anti-inflammatory, a steroid, a steroid hormone, a bronchodilator or a drug used to treat osteoporosis. Additional preferred medicaments include drugs used to treat incontinence, antidepressants/anxiolytics, antimigraine agents, agents used in smoking cessation therapy, antidiarrheals, anticholinergics, anticonvulsants, drugs for mood disorders/obsessive compulsive disorder, ACE inhibitors, calcium channel blockers, antihypertensives/diuretics, anti-obesity drugs, hormonal peptides and analogues, drugs for benign prostatic hyperplasia/urinary retention and erectile dysfunctions, antiparkinson agents such as dopamine agonists and MAO inhibitors, drugs for sleep disorders and antidiabetic agents.

One preferred anti-emetic is scopolamine. Preferred antianginals include nitroglycerine, clonidine, isosorbide dinitrate, propanolol HCl, timolol maleate, clonazepam and verapamil. Preferred anti-inflammatory drugs include diclofenac sodium, naproxen sodium, ibuprofen, ketoprofen, indomethacin, piroxicam, ketorolac, tromethamine and nimesulide. Preferred steroids include hydrocortisone and esters thereof, dexamethasone, fluocinolone acetonide and betamethasone and salts thereof. Preferred hormonal steroids include estradiol or noethisterone and their pharmaceutically acceptable salts or a combination thereof, testosterone or progesterone. Preferred bronchodilators include salbutamol and salts thereof, bambuterol, salmeterol xinafoate, fluticasone propionate, mometasone furoate, budesonide, beclomethasone dipropionate, sodium cromoglycate and isoprenaline sulphate. Preferred drugs used in case of osteoporosis include alendronic acid, pamidronic acid, etidronic acid and their pharmaceutically acceptable salts. Preferred drugs used to treat incontinence include vasopressin and oxybutynin. Preferred antidepressants/anxiolytics include imipramine, mirtazapine and desipramine. Preferred antimigraine agents include naratriptan, zolmitriptan and sumatriptan. One preferred antidiarrheal is loperamide. One preferred antiulcerant is misoprostol. Preferred anticholinergics include hyoscyamine, atropine and trihexyphenidyl. Preferred anticonvulsants include lorazepam, diazepam and tiagabine. Preferred drugs for antimood disorders/obsessive compulsive disorder include fluoxetine and paroxetine. Preferred ACE inhibitors include lisinopril, trandolapril and captopril. Preferred calcium channel blockers include amlodipine and felodipine. Preferred antihypertensives/diuretics include prazosin and amiloride. Preferred antiobesity drugs include methamphetamine and sibutramine hydrochloride. Preferred hormonal peptides and analogues include GnRH analogues such as nafarelin, leuprolide acetate, insulin and growth hormone and analogues thereof. Preferred drugs for benign prostatic hyperplasia/urinary retention include doxazosin, tamsulosin, terazosin and finasteride. Preferred drugs for erectile dysfunction include alprostadil and sildenafil citrate. Preferred antiparkinson agents include dopamine agonists such as bromocriptine and cabergoline and MAO inhibitors such as selegiline HCl. One preferred agent for sleep disorders is melatonin. Preferred antidiabetic agents include first and second generation sulphonyl ureas such as glimepiride, rosiglitazone, glyburide and glipizide. The chiral forms of all the drugs mentioned above, as well as achiral forms, can be used to make the topical spray composition of the present invention.

The film-formers preferably include acrylic polymers or copolymers, including methacrylic polymers and copolymers. Preferred film-formers include a non-ionic copolymer of methyl methacrylate and butyl methacrylate (Plastoid B®), a copolymer of dimethylamine ethyl methacrylate and a neutral methacrylic acid ester (Eudragit E100®), ammonio methacrylate copolymer type B (Eudragit RS®, USP/NF), ammonio methacrylate copolymer type A (Eudragit RL®, USP/NF), methacrylic acid copolymer type A (Eudragit L100®, USP/NF), methacrylic acid copolymer type B (Eudragit S100® USP/NF), polyvinyl acetate, cellulose acetate, polyvinyl alcohol, povidone, povidone vinyl acetate, hydroxypropyl methyl cellulose, hydroxy ethyl cellulose, methyl cellulose and ethyl cellulose.

The breathability of the film is achieved by the absence of any occlusive backing membrane together with the generally hydrophilic properties of the film-forming polymer(s). These polymers can partially dissolve on exposure to moisture (from the skin or air), the dissolution resulting in the formation of a porous film. This porosity can be enhanced by including additional water-soluble additives, such as those detailed below.

Preferred solubilizers include a copolymer of dimethylamine ethyl methacrylate and a neutral methacrylic acid ester (Eudragit E100®, USP/NF); surfactants, for example, sodium lauryl sulphate; polyhydric alcohols, for example, propylene glycol or polyethylene glycol; vitamin E, vitamin E TPGS (tocopheryl polyethylene glycol 1000 succinate) and labrasol; or any two or more of the above in combination. Preferably, the solubilizer is a copolymer of dimethylamine ethyl methacrylate and a neutral methacrylic acid ester (Eudragit E100®) in combination with, a non-ionic copolymer of methyl methacrylate and butyl methacrylate (Plastoid B®). The solubilizers serve to dissolve the drug in the chosen vehicle. Many of the solubilizers also enhance percutaneous penetration of drug and/or act as humectants.

Preferred plasticizers include triethyl citrate, dimethyl isosorbide, acetyltributyl citrate, castor oil, propylene glycol, and polyethylene glycol, or any two or more of the above in combination.

The permeation enhancer is preferably a lipophilic solvent, for example, dimethyl sulfoxide, dimethyl formamide or isopropyl myristate; a surfactant, for example, Tweens or sodium lauryl sulfate; menthol; oleic acid, octyl dimethyl para-amino benzoic acid (Padimate 0); mixed esters of capric and caprylic acid; or a polyhydric alcohol, for example, propylene glycol or diethylene glycol monoethyl ether EP (transcutol); or any two or more of the above in combination.

The vehicle can be water or a non-aqueous solvent. Preferred nonaqueous vehicles include acetone, isopropyl alcohol, methylene chloride, methyl-ethyl-ketone, absolute alcohol, ethyl acetate and trichloromonofluoromethane (P11), methylene dimethyl ether or any two or more of the above in combination.

The aqueous or non-aqueous vehicle may additionally comprise (weight/weight of vehicle) up to 20% of one or more humectants. Preferred humectants include polyhydric alcohols and polyvinyl pyrrolidone. Preferred polyhydric alcohols are propylene glycol, butylene glycol, polyethylene glycol, glycerol and sorbitol.

The water-soluble additive is preferably propylene glycol, sodium lauryl sulphate, one or more polaxomers, polyoxyl 35 castor oil, polyoxyl 40 hydrogenated castor oil, cetomacrogol, polyethylene glycol or transcutol, or any two or more of the above in combination.

When the composition is dispensed as an aerosol, the vehicle partly comprises a propellant in an amount to provide from about 10% to about 90% (w/w) of the composition. The propellant can be any pharmaceutically acceptable propellant which provides a suitable pressure within an aerosol dispenser, preferably a pressure of from about 20 p.s.i.g. to about 130 p.s.i.g. Preferred propellants include hydrocarbons, for example, propane, butane, isobutane, or dimethylether; hydrofluorocarbons and hydrochlorofluorocarbons, for example, dichlorodifluoromethane (P12), trichloromonofluoromethane (P11), dichlorofluoroethane, monochlorodifluoromethane (P22), dichlorotetrafluoroethane (P114), difluoroethane (P152a), tetrafluoroethane (134a), heptafluoropropane (P227b); or compressed gases, for example, nitrogen or carbon dioxide.

The topical compositions of the present invention are quick drying, non-occlusive formulations which cause marked enhancement of the skin permeation of the drug both in vitro and in vivo when compared with existing transdermal patches. They offer the advantages of lower skin irritation, greater ease of use, increased dosage flexibility and a simpler method of manufacture when compared to existing transdermal patches.

The present compositions are a significant advance over conventional medicinal aerosol compositions, since they permit the application of a medicament by a method whereby no physical contact on the area of application is required, except by the film-forming spray itself. The topical films formed by the present compositions show excellent stability and peelability and can be easily removed from the site of application by washing with water.

The compositions are generally prepared by mixing the ingredients, without liquefied propellant, at a temperature of from 0° C. to 100° C. and at ambient pressure. If propellant is to be added, the resulting mixture is then charged with the liquefied propellant into an aerosol dispenser to achieve the final composition. Mixing is preferably carried out at a temperature of from 10° C. to 25° C. Alternatively, the mixed composition is placed in a pump dispenser, for example, a metered dose pump, which dispenses the composition typically without liquefied propellant since a pressurized atmosphere is not required. Propellant which is liquid at room temperature may, however, be included in a pump dispenser composition as part of the aqueous vehicle.

The composition so prepared is sprayed from the dispenser onto a topical site, at which site it forms a stable, plastic film or patch.

The aerosol dispenser is preferably a conventional aerosol can having a conventional metered spray aerosol valve. The pump dispenser is preferably a conventional can or bottle having a conventional metered spray pump. Preferably, the aerosol dispenser has an all position valve having a shroud that permits spraying when the dispenser is held at any angle. In this way, horizontal bottom surfaces, as well as horizontal top surfaces and vertical surfaces, can be sprayed. The valve actuator can be any actuator which produces a spray and not a foam at the nozzle. A preferred valve actuator is a mechanical breakup actuator, which employs mechanical forces rather than expansion and evaporation of the propellant to produce a spray. A typical mechanical breakup actuator has a conical or cylindrical swirl chamber with an inlet channel oriented perpendicular to the axis thereof. This structure imparts a swirling motion to the aerosol mixture upon discharge. The swirling motion occurs around the axis of the swirl chamber forming a thin conical film of discharged mixture, which breaks into droplets as it leaves the swirl chamber and travels in the direction of the axis thereof. The result is a fine, soft, dispersed spray which can be easily controlled to produce a stable thin film of even thickness completely contacting the application site. In dispensing a composition of the invention, the dispenser is typically held about 1 to 2 inches (2.5 to 5 cm) from the application site and produces a film of even thickness. The dispensers used in the present invention are preferably compact units. They can be conveniently used for quick and easy application of a medicament over a large surface area.

The composition is preferably applied over a fixed surface area. Typically, the fixed surface area is not more than 50 cm$^2$, and is more preferably from 10 cm$^2$ to 25 cm$^2$.

In general, a composition according to the present invention suitable for use in an aerosol dispenser can be prepared as follows:
1. Dissolve the film former in the chosen vehicle with stirring to form a clear solution;
2. Dissolve or suspend the active ingredient and solubilizer(s) along with the permeation enhancer, together with any water-soluble additives required, in the solution formed in step 1;
3. Add the plasticizer to the solution and fill a conventional aerosol can with the mixture; and
4. Charge the filled can with liquefied propellant.

The following examples illustrate the preparation of compositions according to the present invention.

Examples 1 and 2 below represent partly generalized formulas which can be used with any suitable medicament to prepare compositions according to the present invention for use in an aerosol dispenser.

EXAMPLE 1

| Ingredients | Percent w/w |
| --- | --- |
| Active ingredient | 0.5–10.0 |
| Plastoid B | 2.25 |
| Eudragit E 100 | 0.25 |
| Propylene glycol | 3.0 |
| Sodium lauryl sulfate | 3.5 |
| Acetone | 20 |
| Propellant | q.s. |
| Vitamin E | 0.1 |
| Transcutol | 1.0 |

EXAMPLE 2

| Ingredients | Percent w/w |
| --- | --- |
| Active ingredient | 15 |
| Povidone | 3 |
| Povidone VA-64 | 2 |
| Vitamin E | 0.5 |
| PEG 400 | 1.0 |
| Propylene glycol | 1.5 |
| Ethanol | 15 |
| Acetone | 15 |
| Propellant | q.s. |

More specific examples of compositions for use in an aerosol dispenser are set forth in Examples 3 through 5.

EXAMPLE 3

| Ingredients | Percent w/w |
| --- | --- |
| Estradiol | 1 |
| PVP-K-30 | 6 |
| PVP VA | 4 |
| Vitamin E | 1 |
| PEG 6000 | 2 |
| Propylene glycol | 3 |
| P12 | 58.1 |
| P11 | 24.9 |

EXAMPLE 4

| Ingredients | Percent w/w |
| --- | --- |
| Estradiol | 2 |
| PVP K-30 | 6 |
| PVP VA | 4 |
| Vitamin E | 1 |
| PEG 6000 | 2 |
| Propylene glycol | 3 |
| P12 | 24.9 |
| P11 | 57.1 |

EXAMPLE 5

| Ingredients | Percent w/w |
| --- | --- |
| Alendronate sodium | 1 |
| PVP K-30 | 6 |
| PVP VA | 4 |

-continued

| Ingredients | Percent w/w |
|---|---|
| Vitamin E | 0.5 |
| Menthol | 0.05 |
| Dimethyl isosorbide | 3.0 |
| Acetone | 10 |
| Ethanol | 10 |
| Tetrafluoroethane (P134) | 25.45 |
| Dichlorodifluoromethane (P12) | 40 |

To prepare a composition according to the present invention suitable for use in a pump dispenser, the general method set forth above for an aerosol dispenser can be used, except that it is not necessary to charge the pump dispenser with liquefied propellant to provide a pressurized atmosphere. The mixture itself may contain propellant which is liquid at room temperature as part of the vehicle.

Examples 6 through 9 represent partly generalized formulas which can be used with any suitable medicament to prepare compositions according to the present invention for use in a pump dispenser.

EXAMPLE 6

| Ingredients | Percent w/w |
|---|---|
| Active ingredient | 0.5–10.0 |
| Plastoid B | 5.6 |
| Eudragit E 100 | 0.6 |
| Propylene glycol | 4.0 |
| Sodium lauryl sulfate | 3.0 |
| Acetone | 20 |
| Isopropyl alcohol | q.s. |
| Vitamin E | 0.2 |
| Transcutol | 2.0 |

EXAMPLE 7

| Ingredients | Percent w/w |
|---|---|
| Active ingredient | 25 |
| Povidone | 6 |
| Povidone VA-64 | 4 |
| Vitamin-E | 1.0 |
| Propylene glycol | 3 |
| Ethanol | 27 |
| Acetone | q.s. |
| Methylene chloride | 27 |

EXAMPLE 8

| Ingredients | Percent w/w |
|---|---|
| Active ingredient | 15 |
| PVP K 30 | 6 |
| PVP VA | 4 |
| Vitamin-E TPGS | 0.5 |
| Dimethyl isosorbide | 5 |

-continued

| Ingredients | Percent w/w |
|---|---|
| Ethanol | 20 |
| Trichloromonofluoromethane (P11) | q.s. |

EXAMPLE 9

| Ingredients | Percent w/w |
|---|---|
| Active ingredient | 0.5–10 |
| PVP VA | 10 |
| Vitamin E | 0.5 |
| Propylene glycol | 3 |
| Ethanol | 25 |
| Trichloromonofluoromethane (P11) | q.s. |

More specific examples of compositions which can be used in a pump dispenser are set forth in Examples 10 through 12.

EXAMPLE 10

| Ingredients | Percent w/w |
|---|---|
| Estradiol | 2 |
| PVP K-30 | 6 |
| PVP VA | 4 |
| Vitamin E | 1 |
| PEG 6000 | 2 |
| Propylene glycol | 3 |
| Acetone | 27 |
| Methylene chloride | 27 |
| Ethanol | 28 |
| Dichlorodifluoromethane (P12) | 40 |

EXAMPLE 11

| Ingredients | Percent w/w |
|---|---|
| Estradiol | 1 |
| PVP K-30 | 6 |
| PVP VA | 4 |
| Vitamin E | 1 |
| PEG 6000 | 2 |
| Polyethylene glycol | 3 |
| Acetone | 27 |
| Methylene chloride | 28 |
| Ethanol | 28 |

EXAMPLE 12

| Ingredients | Percent w/w |
|---|---|
| Estradiol | 1 |
| PVP K-30 | 6 |
| PVP VA | 4 |
| Vitamin E | 1 |
| Menthol | 0.05 |
| Dimethyl isosorbide | 5 |
| Acetone | 27.48 |
| Ethanol | 27.48 |
| P11 | 27.48 |

The following further explanation is given of the above examples. Eudragit E 100 is a self-adhesive, hydrophilic matrix system. It also acts as a solubilizer for the drug Estradiol. Plastoid B is a film-former. When used together, Eudragit E 100 and Plastoid B give better peelability and water washability than when either is used alone. Acetone is a volatile, quick-drying, non-occlusive vehicle which helps to dispense the contents of the spray over a large surface area. Propylene glycol acts as a humectant to prevent the excessive drying of the application site after application of the medicament. It also acts as a plasticizer for the film formed after application. Propylene glycol additionally acts as a solubilizer for the drug and a permeation enhancer. Sodium lauryl sulfate acts as a solubilizer for the drug.

Propellant is necessary for developing proper pressure within an aerosol container and for expulsion of the composition when the valve is open. It is also responsible, together with the valve, for dispensing the product as a fine spray. The preferred propellants are very stable compounds and relatively non-toxic, inert and non-flammable.

The compositions in the above examples were discharged from the dispenser as a fine, soft dispersed spray which could be easily controlled to produce a stable thin film of even thickness on a target surface, for example, a laboratory cover glass. The films have been observed to last for at least 24 hours. The concentrations of the film-formers in the composition can be varied as required to obtain a patch which can deliver the drug in a sustained manner for a period of up to 1 to 5 days. The film is easily removable from the application site by water in preparation for reapplication of the film or other treatment.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. An aerosol spray composition for topical application comprising:
   about 1% Alendronate sodium,
   about 6% povidone,
   about 4% povidone vinyl acetate,
   about 0.5% vitamin E,
   about 0.05% menthol,
   about 3% dimethyl isosorbide,
   about 10% acetone,
   about 10% ethanol,
   about 25.45% tetrafluroroethane and,
   about 40% dichlorodifluoromethane.

2. A sprayable composition for topical ad ministration comprising:
   about 0.5 to about 15% at a medicament,
   about 6% povidone,
   about 4% povidone vinyl acetate,
   about 0.5% vitamin E,
   about 5% dimethyl isosorbide,
   about 20% ethanol and,
   trichloromonfluoromethane.

3. A sprayable composition for topical administration comprising:
   about 1% estradiol,
   about 6% povidone,
   about 4% povidone vinyl acetate,
   about 1% vitamin E,
   about 0.05 menthol,
   about 5% dimethyl isosorbide,
   about 27.5% acetone,
   about 27.5% ethanol and
   about 27.5% trichlomonofluoromethane.

* * * * *